US00PP09120P

United States Patent [19]

Takanashi et al.

[11] Patent Number: Plant 9,120

[45] Date of Patent: Apr. 25, 1995

[54] VARIETY OF LIMONIUM NAMED SUPER LADY

[75] Inventors: Nobuaki Takanashi, Kanagawa; Masayuki Morimoto, Shizuoka, both of Japan

[73] Assignee: Dai-Ichi Plantech Co., Ltd., Tokyo, Japan

[21] Appl. No.: 189,421

[22] Filed: Jan. 27, 1994

[51] Int. Cl.[6] ..... A01H 5/00

[52] U.S. Cl. ..... Plt./68.1

[58] Field of Search ..... Plt. 68.1

*Primary Examiner*—James R. Feyrer

*Attorney, Agent, or Firm*—Webb Ziesenheim Bruening Logsdon Orkin & Hanson

[57] ABSTRACT

A new variety of Limonium is tall with good branching. The petal color is a greenish-yellow. The calyx color is pale purplish-pink. The flowers are long-lasting and the plant is easy to grow. Up to 8 stems flowers can be cut in each year.

1 Drawing Sheet

BACKGROUND OF THE INVENTION

The present invention comprises a new and distinct cultivar of the genus Limonium known by the varietal name 'Super Lady'. The new variety was discovered in a selected breeding program by Messrs. Nobuaki Takanashi and Masayuki Morimoto. The new variety is an innerspecific hybridization between two limonium species. The seed parent was *Limonium sinense* (#6) and the pollen parent was *Limonium sinense* (#5).

The new cultivar was discovered in 1990 at the Dai-Ichi Engei Plantech Co., Ltd., 1101-8, Ueno, Oyama, Sunto, Shizuoka, Japan. The new cultivar was first asexually reproduced by cuttings at Dai-Ichi Engei Plantech Co., Ltd. and has been repeatedly asexually reproduced by cuttings at the same location. It has been found to retain its distinctive characteristics through successive propagation. The climate where the new variety was discovered is generally considered to be a cool climate.

DESCRIPTION OF THE DRAWING

The accompanying colored photograph illustrates the new cultivar, the color being as true as possible with color illustrations of this type.

DESCRIPTION OF THE NEW PLANT

The following detailed description sets forth the characteristics of the new cultivar. The data which defines these characteristics were collected from asexual reproductions grown in an unheated greenhouse during wintertime for bud initiation followed by growth at a temperature of 50° F. The plant histories were taken of plants blossomed under full light in a greenhouse and the color readings were taken under sunlight. Color references are primarily to the RHS Color Chart of The Royal Horticultural Society of London.

THE PLANT

Classification:

*Botanical.*—*Limonium sinense.*

*Commerical.*—Limonium sp.

Form: Mounding.

Growth: Medium, vigor.

Branching: Sparse to moderately dense floral canopy is formed.

Height from soil line: 40 inches.

Spread: 30 inches.

Hardiness: Can tolerate cold, but not heat.

Disease resistance: Average.

Effects of weather: Requires low temperature and less than 40° for bud initiation. Plant becomes perennial and does not produce flowering stems if not exposed to low temperature.

Suitability of panicles for drying: Good.

Cutting: 8 flowering stems are produced under normal temperature conditions. Up to 15 flowering stems are produced when a young plant is exposed to low tempertaures for about two months. Plant dies after low temperature treatment.

THE BUD

Size: 0.8 inches in diameter; 0.24 inches in length.

Rate of opening: Greater than 80%.

Petals:

*Visibility.*—Not within view; packed with sepals.

*Petals.*—Yellow Group 6A.

*Sepals.*—Green Group 143C.

INFLORESCENCE

Fully expanded: 30 inches.

Stems: 40 inches.

Form: Panicle.

Performance: Long lasting.

Color:

*Tonality from a distance.*—Greenish-yellow petals and pale purplish-pink calyx.

*Front of petals.*—Yellow Group 3A.

*Reverse of petals.*—Yellow Group 3A.

*Base of petals.*—Yellow-Green Group 155D.

*Throat.*—Green Group 137B.

*Discoloration.*—Does not fade.

Petals:

*Dimensions.*—4.0 mm wide, 5.7 mm long.

*Texture.*—Thin.

*Appearances.*—Five pieces, polypetal, all petals have the same shape.

*Arrangement.*—Radial.

*Persistance.*—Good.

*Fragrance.*—Mild.

Sepals:

*Color.*—Front — Red-Purple Group 65C. Reverse — Red-Purple Group 65D.

*Dimensions.*—5.8 mm wide, 6.0 mm long.
*Shape.*—Pentagonal.

REPRODUCTIVE ORGANS

Anthers: 0.04 inch, Green-Yellow Group 1D.
Stamen: 0.31 inches.
Filament: 0.27 inches and White Group 155D.
Ovaries: 0.04 inches and Yellow-Green Group 145C.
Pollen: Very little.
Stigma: Extremely small and thin when present and generally not detectable.
Pistils: 0.22 inches.
Foliage:

*Size.*—10 inches in length; 2.5 inches in width.
*Form.*—Rosette.
*Quantity.*—50–60 leaves per plant.
*Shape.*—Oblong — spatulate. Top side: Roguse. Underside: Roguse.
*Rib and vein color.*—Green Group 139D.
*Margin.*—Wavy and entire.

We claim:

1. A new and distinct variety of Limonium as shown and described herein and characterized by its greenish-yellow petals, pale purplish-pink calyx, height, and good branching.

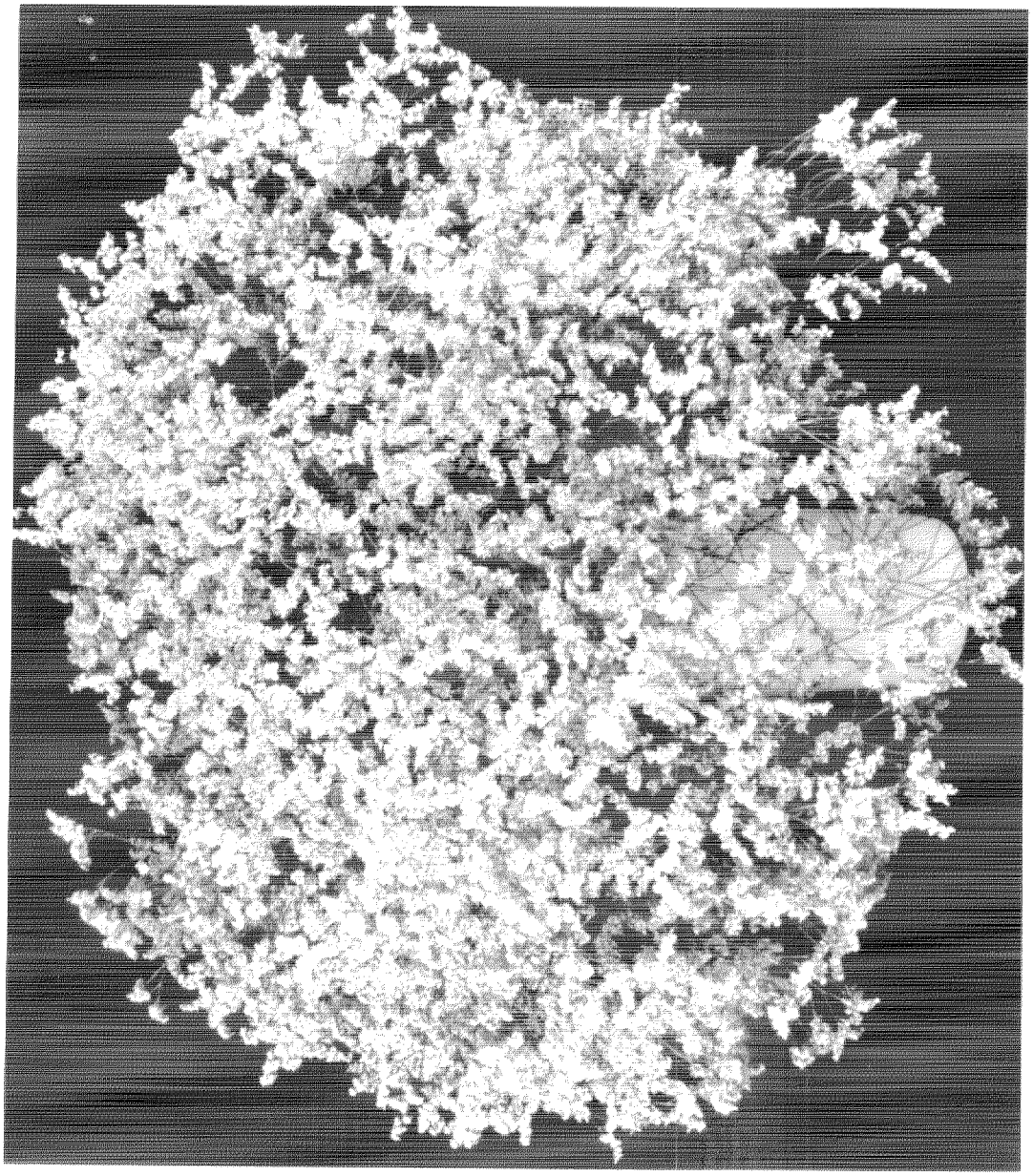

* * * * *